(12) United States Patent
Wallace et al.

(10) Patent No.: US 6,602,269 B2
(45) Date of Patent: Aug. 5, 2003

(54) EMBOLIC DEVICES CAPABLE OF IN-SITU REINFORCEMENT

(75) Inventors: Michael P. Wallace, Fremont, CA (US); Stephen Christopher Porter, Fremont, CA (US)

(73) Assignee: SciMed Life Systems, Maple Grove, MN (US)

( * ) Notice: Subject to any disclaimer, the term of this patent is extended or adjusted under 35 U.S.C. 154(b) by 47 days.

(21) Appl. No.: 09/822,918

(22) Filed: Mar. 30, 2001

(65) Prior Publication Data

US 2002/0143348 A1 Oct. 3, 2002

(51) Int. Cl.[7] .............................................. A61M 29/00
(52) U.S. Cl. ...................................................... 606/191
(58) Field of Search ................................ 606/108, 191, 606/192, 194, 195, 198, 200, 213; 604/30, 49, 52, 53, 96, 104, 264, 523

(56) References Cited

U.S. PATENT DOCUMENTS

| 4,994,069 A | 2/1991 | Ritchart et al. |
|---|---|---|
| 5,122,136 A | 6/1992 | Guglielmi et al. |
| 5,226,911 A | 7/1993 | Chee et al. |
| 5,234,437 A | 8/1993 | Sepetaka |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford et al. |
| 5,312,415 A | 5/1994 | Palermo |
| 5,350,397 A | 9/1994 | Palermo et al. |
| 5,354,295 A | 10/1994 | Guglielmi et al. |
| 5,356,388 A | 10/1994 | Sepetka et al. |
| 5,382,259 A | 1/1995 | Phelps et al. |
| 5,462,523 A | 10/1995 | Samson et al. |
| 5,536,274 A | 7/1996 | Neuss |
| 5,658,308 A | 8/1997 | Snyder |
| 5,669,931 A | 9/1997 | Kupiecki |
| 5,690,666 A | 11/1997 | Berenstein et al. |
| 5,690,671 A | 11/1997 | McGurk et al. |
| 5,749,894 A * | 5/1998 | Engelson .................... 128/898 |
| 5,826,587 A | 10/1998 | Berenstein et al. |
| 5,980,550 A | 11/1999 | Eder et al. |
| 6,015,424 A | 1/2000 | Rosenbluth et al. |
| 6,146,373 A | 11/2000 | Cragg et al. |
| 6,299,619 B1 * | 10/2001 | Greene et al. .............. 606/108 |
| 2001/0047202 A1 * | 11/2001 | Slaikeu et al. ............. 623/1.46 |

OTHER PUBLICATIONS

Dondelinger et al., Embolization Materials ed., *Interventional Radiology*, Thieme, N.Y. 295–313 (1990).

Herrera et al., "Histological Changes in the Rat Common Carotid Artery Induced by Aneurysmal Wrapping and Coating Materials," *Neurol. Med. Chir.* (Tokyo) 39(2):134–139 (1999).

(List continued on next page.)

*Primary Examiner*—John J. Calvert
*Assistant Examiner*—Shaun R Hurley
(74) *Attorney, Agent, or Firm*—Robins & Pasternak LLP

(57) ABSTRACT

Described herein are embolic assemblies that can be reinforced in situ. In particular, assemblies are described comprising (i) an implantable device designed to allow injection of a liquid agent through the lumen of the device or a lumen defined by the device and (ii) an implantable device and a liquid agent, wherein the liquid agent is capable of solvating polymeric material of the device. Methods of making and using these assemblies are also provided.

9 Claims, 1 Drawing Sheet

OTHER PUBLICATIONS

Mandai et al., "Direct Thrombosis of Aneurysms With Cellulose Acetate Polymer," *J. Neurosurgery* 77:497–500 (1992).

Moringlane et al., "Experimental Aneurysms in the Rabbit: Occlusion by Intrasaccular Injection of Fibrin Sealant," *Surg Neurol.* 28(5):361–366 (1987).

Moringlane et al., "Occlusion of Experimental Artery Aneurysms by Intrasaccular Injection of Fibrin Sealant," *Acta Neurochirugica Suppl.* (Wein) 43:193–197 (1988).

Murayama et al., "Development of the Biologically Active Guglielmi Detachable Col for the Treatment of Cerebral Aneurysm. Part II: An Experimental Study in a Swine Aneurysm Model," *American J. Neuradiol.* 20(10):1992–1999 (1999).

Suga et al., "Fibrin Glue, Aneurysmal Occlusion, Angioplastic Ballon," *No Shinkei Geka* 20(8):865–873 (1992).

Sugawara et al., "Experimental Investigations Concerning a New Liquid Embolization Method Combined Administration of Ethanol–estrogen and Polyvinyl Acetate," *Neuro Med Chir* (Tokyo) 33:71–76 (1993).

Taki et al., "A New Liquid Material for Embolization of Arteriovenous Malformations," *Am. J. Neuroradial* 11:163–168 (1990).

Vinters et al., "The Histotoxicity of Cyanoacrylates," *Neuroradiology* 27:279–291 (1995).

* cited by examiner

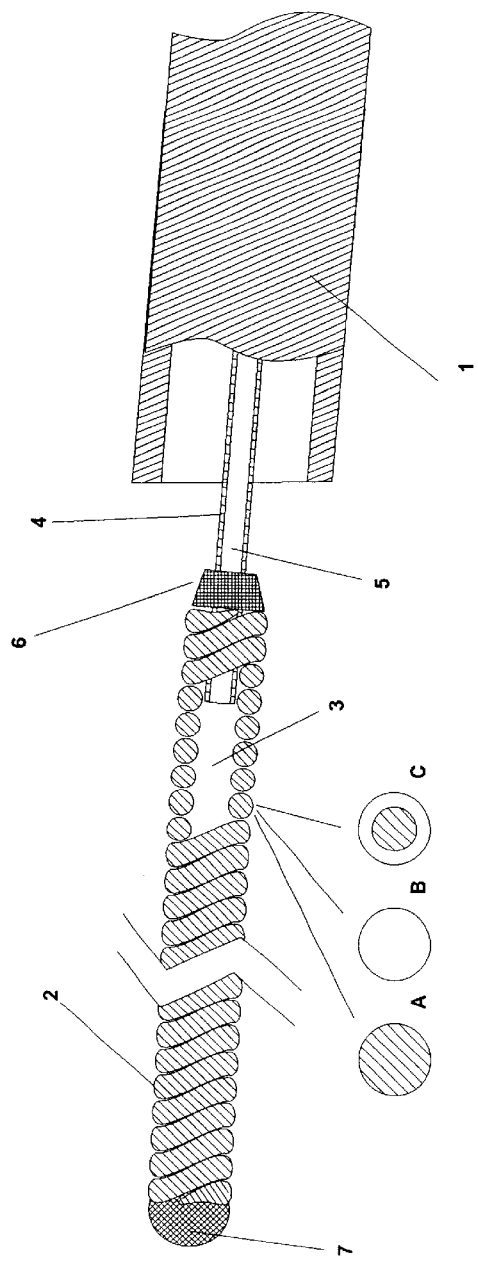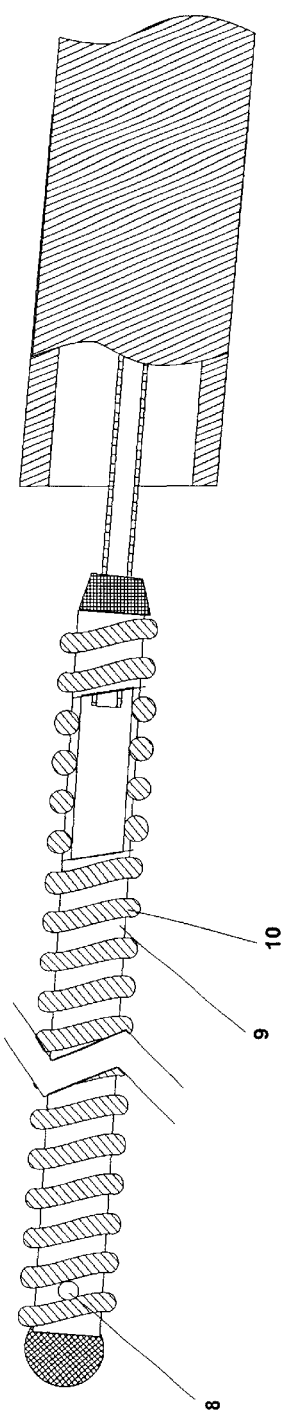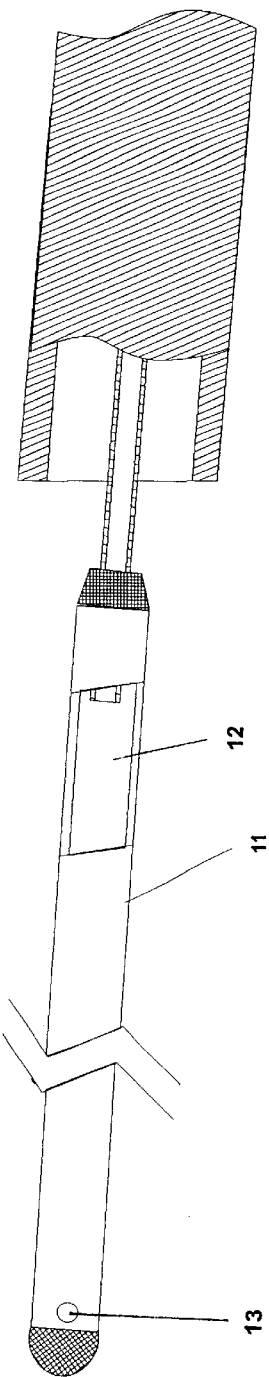

EMBOLIC DEVICES CAPABLE OF IN-SITU REINFORCEMENT

FIELD OF THE INVENTION

Compositions and methods for repair of aneurysms are described. In particular, embolic devices that allow the operator to deliver and transform in situ embolic material.

BACKGROUND

An aneurysm is a dilation of a blood vessel (similar to a balloon) that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. (See, e.g., U.S. Pat. No. 4,994,069 to Ritchart et al.) Other less stiff helically coiled devices have been described, as well as those involving woven braids.

U.S. Pat. No. 5,354,295 and its parent, U.S. Pat. No. 5,122,136, both to Guglielmi et al., describe an electrolytically detachable embolic device. Modified GDC coils have also been used in aneurysms, for example surface-modified GDCs as described in Murayama et al. (1999) *American J Neuradiol* 20(10):1992–1999. Vaso-occlusive coils having little or no inherent secondary shape have also been described. For instance, coowned U.S. Pat. No. 5,690,666 and 5,826,587 by Berenstein et al., describes coils having little or no shape after introduction into the vascular space.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vasoocclusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

In addition, several patents describe deployable vaso-occlusive devices that have added materials designed to increase their thrombogenicity. For example, fibered vasoocclusive devices have been described at a variety of patents assigned to Target Therapeutics, Inc., of Fremont, Calif. Such vaso-occlusive coils having attached fibers is shown in U.S. Pat. Nos. 5,226,911 and 5,304,194, both to Chee et al. Another vasoocclusive coil having attached fibrous materials is found in U.S. Pat. No. 5,382,259, to Phelps et al. The Phelps et al. patent describes a vaso-occlusive coil which is covered with a polymeric fibrous braid on its exterior surface. U.S. Pat. No. 5,658,308 to Snyder is directed to a coil having a bioactive core. The coils may be coated with agarose, collagen or sugar. U.S. Pat. No. 5,669,931 to Kupiecki discloses coils that may be filed or coated with thrombotic or medicinal material. U.S. Pat. No. 5,749,894 to Engleson discloses polymer coated vaso-occlusion devices. U.S. Pat. No. 5,690,671 to McGurk discloses an embolic element which may include a coating, such as collagen, on the filament surface.

U.S. Pat. No. 5,536,274 to Neuss shows a spiral implant which may assume a variety of secondary shapes. Some complex shapes can be formed by interconnecting two or more of the spiral-shaped implants. To promote blood coagulation, the implants may be coated with metal particles, silicone, PTFE, rubber latices, or polymers. U.S. Patent No. 5,980,550 describes a vaso-occlusive device having a bioactive inner coating and a water-soluble outer coating. Co-owned WO/027445, titled "Bioactive Coating for Vaso-occlusive Devices," describes vaso-occlusive devices coated with a collagen-based material and, additionally, describes the use of a tie-layer between the device and the collagen-based coating.

Liquid embolics, such as cyanoacrylate glues and fibrin sealants, have also been used in animal and human subjects. See, e.g., Interventional Radiology, Dandlinger et al, ed., Thieme, N.Y., 1990:295–313; Suga et al. (1992) *No Shinkei Geka* 20(8):865–873; Moringlane et al. (1987) *Surg Neurol* 28(5):361–366; Moringlane et al. (1988) *Acta Neurochir Suppl.* (Wein) 43:193–197. Of these liquid embolics, cyanoacrylate glues are the only liquid embolics currently available to neurosurgeons. However, chronic inflammation is typically seen with cyanoacrylate. treatments (Herrera et al. (1999) *Neurol Med Chir* (Tokyo) 39(2):134–139) and the degradation product, formaldehyde, is highly toxic to the neighboring tissues. See, Vinters et al (1995) *Neuroradiology* 27:279–291. Another disadvantage of cyanoacrylate materials is that the polymer will adhere both to the blood vessel and to the tip of the catheter. Thus physicians must retract the catheter immediately after injection of the cyanoacrylate embolic material or risk adhesion of the cyanoacrylate and the catheter to the vessel.

Another class of liquid embolic materials--precipitative materials--was invented in late 80's. See, Sugawara et al (1993) *Neuro Med Chir* (Tokyo) 33:71–76; Taki et al (1990) AJNR 11:163–168; Mandai et al (1992) *J Neurosurgery* 77:497–500. Unlike cyanoacrylate glues which are monomeric and rapidly polymerize upon contact with blood, precipitative materials are pre-polymerized chains that precipitate into an aggregate upon contact with blood. One potential problem in using the precipitating polymers is the use of organic solvents to dissolve the polymers, i.e., ethanol for PVAc and DMSO for EVAL and CA. These materials are strong organic solvents that can dissolve the catheter hub, and, in the case of DMSO, can damage microcapillary vessels and surrounding tissues. These solvents are also known to cause vasospasm of blood vessels. Additionally, these precipitating agents are often difficult to deliver and typically require the use of multi-lumen catheters (see, e.g., U.S. Pat. No. 6,146,373).

U.S. Pat. No. 6,015,424 describes a vascular embolization device comprising an elongate filamentous element that is control lably transformable from a soft, compliant state to a rigid or semi-rigid state after deployment, for example by contact with blood.

None of the currently available devices approximates the design and functional characteristics of the device described below.

SUMMARY OF THE INVENTION

Thus, this invention includes novel occlusive compositions as well as methods of using and making these compositions.

In one aspect, the invention includes a vaso-occlusive assembly, comprising (a) an implantable device having an axial lumen and (b) a liquid agent, wherein the liquid agent is infused into the lumen of the implantable device, and further wherein the liquid agent (i) self-polymerizes into a rigid or semi-rigid state after infusion (e.g., over a period of minutes to hours) or (ii) polymerizes upon interaction with one or more additional agents disposed in the lumen of the implantable device. The liquid agent can be any suitable substance, for example, fibrin, fibrinogen, thrombin, collagen, polyethylene glycol, cyanoacrylate, microcrystalline wax compositions, cellulose acetate polymers, plasticizers and combinations of two or more of these materials. The liquid agent can be infused into the lumen of the implantable device after deployment of the device or, alternatively, can be infused into the lumen of the device prior to deployment. Further, the implantable device can be a vaso-occlusive coil or other device.

In certain embodiments, the liquid agent self-polymerizes over a period of minutes to hours. In other embodiments, the liquid agent polymerizes to a rigid or semirigid state upon contact with the one or more additional elements, for example, thrombin or calcium. The additional element required for polymerization can be disposed within the axial lumen prior to deployment or, alternatively, after deployment. Any of the assemblies described herein can further comprise a flexible tubular pusher operably linked to the lumen of the device and/or a radio-opaque material. The radio-opaque material can be integrated into, the device and/or into the liquid agent, additional element or any combination thereof.

In another aspect, the invention includes a vaso-occlusive assembly, comprising (a) an implantable device comprising a polymeric material and (b) a liquid agent capable of at least partially solvating the polymeric material of the implantable device. In certain embodiments, the liquid agent is at least partially miscible with blood. In any of these aspects, the assembly can further include a radio-opaque material in the implantable device and/or in the liquid agent. The radio-opaque material is preferably at least partially miscible with blood and at least partially miscible with the liquid agent.

Any suitable polymeric material can be used for the implantable device, for example, polyesters, polyethers, polyamides, polyfluorocarbons, polyethyleneterephthalate, polyurethanes, polyacrylics, polyvinyl acetate, cellulose acetate, polyvinyl alcohols, polylactide, polyglycolide, poly (lactide-co-glycolide), poly(e-caprolactone), poly(p-dioxanone), poly(lactide-co-trimethylene carbonate), polyhydroxybutyrate, polyhydroxyvalerate, polyanhydrides, polyortoesters or combinations of one or more of these materials. In certain embodiments, the polymeric material is coated onto the surface of the implantable device.

In any of the assemblies described herein, the liquid agent can be, for example, propylene glycol, polyethylene glycols, ethanol, dimethyl sulfoxide, N-methyl-2-pyrrolidone, glycoflirol, Solketal, glycerol formal, acetone, tetrahydrofurfuryl alcohol, diglyme, dimethyl isosorbide, ethyl lactate or combinations thereof.

Methods of occluding a body cavity comprising introducing any of the assemblies described herein also form an aspect of the invention. In certain embodiments, the liquid agent is infused after deployment of the implantable device. In other embodiments, the liquid agent is infused prior to deployment of the implantable device. In embodiments in which the liquid agent comprises a solvating agent, the methods can serve to fuse the implantable device to itself or to one or more additional devices upon re-solidification of the solvated polymeric material.

These and other embodiments of the subject invention will readily occur to those of skill in the art in light of the disclosure herein.

BRIEF DESCRIPTION OF THE DRAWINGS

FIG. 1 depicts one exemplary embodiment of the present invention. Coil structure 2 is shown attached to pusher element 4 and microcatheter 1. Part of the coil 2 is shown in cross-section, where A shows a metallic coil; B shows a polymer coil; and C shows a metallic coil coated with a polymer. The coil 2 is depicted with a rounded tip 7.

FIG. 2 shows another embodiment comprising a coil 10 and a polymer tube 9 with a lumen. Luminal connections are depicted 8. The coil may be metal, polymer or a hybrid metal-polymer.

FIG. 3 shows yet another embodiments comprising a polymer tube 11 with a lumen therein.

DESCRIPTION OF THE INVENTION

Occlusive (e.g., embolic) compositions are described. In particular, assemblies are described comprising an implantable device designed to allow injection of a liquid agent through the lumen of the device or a lumen defined by the device. The liquid agent is capable of transforming into a solid form, for example, slowly over time or by reaction with an agent already present in the luminal portion of the device. In addition, assemblies and methods are described comprising an implantable device and a liquid agent, wherein the liquid agent is capable of solvating polymeric material of the device. By partially solvating polymeric materials of the implantable device, when these polymeric materials re-solidify the implantable devices can be bonded to themselves and/or to other implantable devices. The compositions described herein find use in vascular and neurovascular indications and are particularly useful in treating aneurysms, for example small-diameter, curved or otherwise difficult to access vasculature, for example cerebral aneurysms. Methods of making and using these devices also an aspects of this invention.

Advantages of the present invention include, but are not limited to, (i) promoting healing of aneurysms; (ii) providing the ability to modify the occlusion properties of a vaso-occlusive device in situ; (iii) reducing the risk of coil compaction; and (iv) improving treatment of aneurysms.

All publications, patents and patent applications cited herein, whether above or below, are hereby incorporated by reference in their entirety.

It must be noted that, as used in this specification and the appended claims, the singular forms "a", "an"; and "the" include plural referents unless the content clearly dictates otherwise. Thus, for example, reference to "a coil" includes a mixture of two or more such devices and the like.

In one aspect, the invention includes an assembly for delivering an implantable embolic device and/or a liquid agent. Typically, the implantable embolic device is delivered through a microcatheter that includes, for example, an axial lumen and a deployment tube that is insertable through this lumen. Suitable microcatheters are known and are commercially available, for example as described in U.S. Pat. No. 6,030,369 and documents cited therein. The microcatheter is selected such that the proximal end is adapted to receive a source of the liquid agent. Preferably, one or more regions, for example the distal end, of the microcatheter is made of a radioopaque material to facilitate visualization of the catheter within a subject. Suitable radio-opaque materials are known to those of skill in the art and include, by way of example, materials such as powdered tantalum, powdered tungsten, bismuth oxide, barium sulfate, and the like.

The implantable embolic device comprises any known vaso-occlusive devices approved for use as implants in the body or could be so approved. Vaso-occlusive coils useful in the practice of the present invention are described, for example, in U.S. Pat. 4,994,069; 5,133,731; 4,226,911; 5,312,415; 5,382,259; 5,382,260; 5,578,074 and 5,718,711. The embolic devices may be made of metallic materials, polymers or combinations thereof. Suitable metals and alloys for the wire making up the primary coil include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy.

The implantable device may also be of any of a wide variety of stainless steels if some sacrifice of radiopacity may be tolerated. Very desirable materials of construction, from a mechanical point of view, are materials which maintain their shape despite being subjected to high stress. Certain "super-elastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire. If a super-elastic alloy such as nitinol is used in the device, the diameter of the coil wire may be significantly smaller than that used when the relatively more ductile platinum or platinum/tungsten alloy is used as the material of construction.

As noted above, the device may also comprise one or more suitable polymers for example, polyethylene, polyacrylics, polypropylene, polyvinylchloride, polyamides such as Nylon, polyurethanes, polyvinylpyrrolidone, polyvinyl alcohols, polyvinylacetate, cellulose acetate, polystyrene, polytetrafluoroethylene, polyesters such as polyethylene terephthalate (Dacron), polylactide, polyglycolide, poly(lactide-co-glycolide), poly(e-caprolactone), poly(p-dioxanone), poly(lactide-co-trimethylene carbonate), polyhydroxybutyrate, polyhydroxyvalerate, polyanhydrides, polyorthoesters, silk, cotton,. and the like. When the polymers are fibrous, they are often looped or tufted. Although it is not critical to this invention, they are usually assembled in bundles of 5 to 100 fibers per bundle. Preferred materials for the polymer component of vaso-occlusive devices comprise polyesters, polyethers, polyamides, and polyfluorocarbons. Especially preferred is polyethyleneterephthalate, sold as Dacron.

In one aspect, the implantable devices described herein comprise a lumen into which a liquid agent can be injected. The lumen can be hollow or partially hollow (e.g, can include one or more additional elements), so long as there is sufficient space for the addition of the liquid agent. In preferred embodiments, the liquid agent is infused into the lumen along the entire length of the coil. However, the concentration and/or amount of the liquid agent need not be constant along the length of the device. Thus, the liquid agent can be infused in (or travel to) specific regions along the length of the device. Additionally, if the device has been manufactured such that one or both ends are sealed, it may be necessary to access the lumen of such sealed devices (e.g., by creating holes in the sealed ends) by any mechanical, chemical or other means.

In yet other embodiments, the implantable device described herein defines a channel or void spaces into which the liquid agent can be infused. For instance, the implantable device may be in the shape of a coil, the interior of which defines a space into which a liquid agent can be infused, for instance as shown in FIG. 1. FIG. 1 depicts exemplary embodiment in which the implantable device comprises a coil structure 2 attached via a pusher element 4 to a microcatheter 1. Shown in cross-section is the luminal space 3 defined by the coil 2. The pusher element also comprises a lumen 5. Also shown in cross-section are individual winds of the coil depicting coils made of metal A, polymer(s) B, or polymer coated metal C. A detachment junction 6, for example a junction that can be detached by application of electrolytic, mechanical, thermal and/or light energy is also shown.

In any of the embodiments described herein, it is desirable that a means for the liquid agent to communicate with the lumen be provided. In this way, the operator can control infusion of the liquid agent. In certain embodiments, a flexible tubular pusher (e.g, hypo-tube) is used to infuse the liquid agent into the lumen of the device. Thus, the assembly preferably comprises communication means to allow injection a liquid agent after the implantable device is deployed. In embodiments where the implantable device comprises a lumen, the liquid agent is preferably in communication with the lumen (for example via the proximal end of the device) to allow the displacement of internally trapped liquids (blood, saline, contrast media, etc.) or air when the liquid agent is injected through the hypo-tube pusher. Alternatively, the communications may be voids or spaces between the winds of a coil device or a distal opening in tubular implantable member, as shown for example in FIG. 2, wherein luminal communication 8 between a polymer, metal or polymer-metal hybrid device 10 and a polymer tube 9 having a lumen therein.

FIG. 3 shows another example of a suitable device with a lumen 12 and luminal communication 13. The structure defining the lumen is depicted in FIG. 3 has a polymeric tube 11. It will be readily apparent that tube-like structures may have one or more luminal communications and/or one or more surface modifications such as holes, perforations or the like. Thus, helical, braided and/or tube-like structures, with or without one or more perforations or holes, can be used. It is further within the scope of this invention that the resorbable vaso-occlusive device comprise shapes or structures other than coils, braids and tubes, for examples, spheres, ellipses, spirals, figure-8 shapes, etc. Furthermore, any of these structures may optionally be designed to include with a lining or coating (e.g., one or more polymers) to help define a lumen. The lining or coating preferably contains one or more luminal connections, for example as shown in FIG. 2 and FIG. 3.

It will also be apparent that the liquid agent can be infused into the lumen (e.g., a lumen within the device or defined by the device) at any point during construction of the device. In certain embodiments, the liquid agent is infused after the implantable device is deployed in the target vessel. In other embodiments, for example, those in which the liquid agent self-polymerizes over a period of time, infusion may take place prior to deployment, for example, as the device is loaded into a catheter for delivery.

In one aspect of the invention, the liquid agent comprises a polymerizing substance, also referred to as a stiffening agent or a liquid embolic. Any suitable stiffening agent(s) can be used and refers to any agent capable of acting as an occlusive agent which is in fluid form at some point during delivery and which fully or partially solidifies (e.g., to a semi-rigid or rigid state). Thus, the term includes particulate materials (e.g., granules, beads, microspheres, etc.) that can be administered in an aqueous solution or in suspension. Liquid adhesives and sealants (e.g., embolics) have been approved for use to control bleeding during surgery. (see, e.g., two-component fibrin glue systems described in WO 92/13495). However, described herein is the use of these and other liquid embolics for occluding aneurysms, for example aneurysms located in tortuous pathways or small-diameter aneurysms. In certain embodiments, the liquid embolic comprises fibrin. Fibrin-containing compositions are commercially available, for example from Baxter. Collagen containing compositions are commercially available, for example from Cohesion Technologies, Inc., Palo Alto, Calif. Fibrinogen-containing compositions are described, for example, in U.S. Pat. Nos. 6,168,788 and 5,290,552. In other embodiments, the liquid embolic comprises one or more polyethylene glycol (PEG) derivatives, for example PEG derivatives available from Cohesion Technologies, Inc., Palo Alto, Calif. Thrombin-containing materials (e.g., thrombin coated gelatin granules, available for example from Fusion) and iron-containing materials (e.g., balloons coated with iron microspheres), also find use in the present invention. These liquid embolic materials can be used alone or in any combination. Other suitable liquid agents (e.g., microcrystalline wax compositions; cellulose acetate polymers and plasticizers, etc.) are described, for example, in U.S. Pat. No. 6,015,424 and the documents cited therein.

Thus, the stiffening liquid agent(s) may be self-polymerizing or, alternatively, polymerization may require the interaction with one or more additional elements. The additional elements required for polymerization may be pre-disposed within the lumen of the device or, alternatively, can be injected concurrently or subsequently to the liquid agent(s). Suitable multi-component polymerizing systems are known in the art, for example it is known that fibrin glues often require activation with thrombin to solidify and form a clot as described in WO 92/13495.

The liquid agents (e.g., liquid embolics) can also be used in combination with additional materials, such as bioactive materials. In certain embodiments, the liquid agent is used in combination with a radio-opaque material, preferably a radio-opaque material that is miscible with the liquid agent and/or blood. In this way, the operator can readily determine, for example, using convention visualization techniques such as X-ray visualization, the amount of, and/or rate at which, the liquid agent is being injected into the device and/or subject.

The devices, assemblies and methods described herein may also include one or more bioactive materials. The term "bioactive" refers to any agent which exhibits effects in vivo, for example a thrombotic agent, a therapeutic agent or the like. Non-limiting examples of bioactive materials include cytokines; extracellular matrix molecules (e.g., collagen); trace metals (e.g., copper); and other molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1) or the like). Non-limiting examples of cytokines which may be used alone or in combination in the practice of the present invention include, basic fibroblast growth factor (bFGF), platelet derived growth factor (PDGF), vascular endothelial growth factor (VEGF), transforming growth factor beta (TGF-$\beta$) and the like. Cytokines, extracellular matrix molecules and thrombus stabilizing molecules (e.g., Factor XIII, PAI-1, etc.) are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additionally, bioactive polypeptides can be synthesized recombinantly as the sequence of many of these molecules are also available, for example, from the GenBank database. Thus, it is intended that the invention include use of DNA or RNA encoding any of the bioactive molecules. Furthermore, it is intended, although not always explicitly stated, that molecules having similar biological activity as wild-type or purified cytokines, extracellular matrix molecules and thrombus-stabilizing proteins (e.g., recombinantly produced or mutants thereof) and nucleic acid encoding these molecules are intended to be used within the spirit and scope of the invention. Further, the amount and concentration of liquid embolic and/or other bioactive materials useful in the practice of the invention can be readily determined by a skilled operator and it will be understood that any combination of materials, concentration or dosage can be used, so long as it is not harmful to the subject.

In yet other preferred embodiments of the invention, the implantable device comprises a polymeric material capable of being controllably and at least partially solvated (or plasticized) and, subsequently, re-solidifying. In these embodiments, the liquid agent comprises a substance that acts to at least partially solvate (or dissolve) the implantable device such that the device can then be bonded to itself (e.g., the individual winds of a coil) or bonded to another implantable device which has been similarly solvated. Suitable solvating agents include, but are not limited to, propylene glycol, polyethylene glycols, ethanol, dimethyl sulfoxide, -methyl-2-pyrrolidone, glycofurol, Solketal, glycerol formal, acetone, tetrahydrofurfuryl alcohol, diglyme, dimethyl isosorbide, and ethyl lactate.

As with embodiments wherein the liquid agent comprises a stiffening agent, the solvating liquid agents of these embodiments, may be infused into the lumen of the device or into a lumen defined by the device, for example the lumen created by a coil. Additionally, the solvating liquid agent can be delivered separately from the implantable device, for example, using a different delivery system after deployment of the device.

Thus, the selection of suitable liquid agents for the desired purpose is within the purview of the skilled artisan in view of the teachings herein. In certain instances, this selection may take into account the miscibility of the liquid agent, particular its miscibility with blood. For example, when the liquid agent comprises a stiffening agent, it may be desirable to employ a liquid agent that is immiscible or only partially miscible in blood and/or in any additional components of the system. Alternatively, in embodiments where the liquid agent comprises a solvating agent, it may be preferred in certain embodiments to employ a liquid agent that is partially to completely miscible in blood and/or additional in additional components, for example radio-opaque or other bioactive agents.

It will be readily apparent that in these aspects of the invention, the implantable device(s) comprises a material (such as a polymer) that can change soften and harden without causing toxic effects in the subject. In certain embodiments, the material (e.g, polymer) to be solvated is coated onto the surface of the device(s) while in other embodiments, the implantable device is made up of such a softenable material. Any of the shapes or structures of implantable devices described herein are also suitable for use lin these embodiments.

The assemblies and devices herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place implantable device at the target site but yet with a sufficient portion of the distal end of the delivery mechanism protruding from the distal end of the catheter to enable detachment of the implantable device. For use in peripheral or neural surgeries, the delivery mechanism will normally about 100–200 cm in length, more normally 130–180 cm in length. The diameter of the delivery mechanism is usually in the range of 0.25 to about 0.90 mm. Briefly, the occlusive devices (and attached means of communicating with the liquid agent to be infused) described herein are typically loaded into a carrier for lintroduction into the delivery catheter and introduced to the chosen site using the procedure outlined below. This procedure may be used in treating a variety of maladies. For instance, in treatment of an aneurysm, the aneurysm itself may be filled with the embolics which cause formation of an emboli and, at some later time, is at least partially replaced by neovascularized collagenous material formed around the implanted devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the implantable device at the distal end, is advanced through the catheter. The device is advanced past the distal end of the catheter and positioned or extruded precisely at the desired treatment site. The liquid agent is preferably infused after extrusion, but, in some embodiments, may be infused earlier during the deployment procedure, for example when the implantable device is introduced into the catheter.

Once the selected site has been reached, the resorbable device is extruded, for example by loading onto a pusher wire. Preferably, the device is loaded onto the pusher wire via a mechanically, electrolytically, thermally or light-cleavable junction (e.g., a GDC-type junction that can be severed by application of heat, electrolysis, electrodynamic activation or other means). Additionally, the device can be designed to include multiple detachment points, as described in co-owned U.S. patent application titled "LIGHT-ACTIVATED MULTI-POINT DETACHMENT MECHANISM". Once the devices and/or liquid agents are held in place by gravity, shape, size, volume, magnetic field or combinations thereof. As noted above, the order in which the components of the vaso-occlusive composition (e.g., liquid agent(s); implantable device; and/or other bioactive materials) are released from the catheter can be determined by the operator.

Modifications of the procedure and device described above, and the methods of using them in keeping with this invention will be apparent to those having skill in this mechanical and surgical art. These variations are intended to be within the scope of the claims that follow.

We claim:

1. A vaso-occlusive assembly, comprising
   (a) an implantable device comprising a polymeric material and
   (b) a liquid agent capable of at least partially solvating the polymeric material of the implantable device.

2. The assembly of claim 1, wherein the liquid agent is at least partially miscible with blood.

3. The assembly of claim 2, further comprising a radio-opaque material.

4. The assembly of claim 3, wherein the radio-opaque material is at least partially miscible with blood and at least partially miscible with the liquid agent.

5. The assembly of claim 1, wherein the polymeric material is selected from the group consisting of polyesters, polyethers, polyamides, polyfluorocarbons, polyethyleneterephthalate, polyurethanes, polyacrylics, polyvinyl acetate, cellulose acetate, polyvinyl alcohols, polylactide, polyglycolide, poly(lactide-co-glycolide), poly(ecaprolactone), polyp-dioxanone), poly(lactide-co-trimethylene carbonate), polyhydroxybutyrate, polyhydroxyvalerate, polyanhydrides, and polyortoesters.

6. The assembly of claim 1, wherein the liquid agent is selected from the group consisting of propylene glycol, polyethylene glycols, ethanol, dimethyl sulfoxide, N-methyl-2-pyrrolidone, glycofuirol, Solketal, glycerol formal, acetone, tetrahydrofuirfitryl alcohol, diglyme, dimethyl isosorbide, and ethyl lactate.

7. The assembly of claim 1, wherein the polymeric material is coated onto the surface of the implantable device.

8. A method of occludina body cavity comprising introducing an assembly comprising (a) an implantable device comprising a polymeric material and (b) a liquid agent capable of at least partially solvating the polymeric material of the implantable device into the body cavity.

9. The method of claim 8, wherein when the polymeric material solidifies, the implantable device is thereby fused to one or more additional devices or to itself.

* * * * *